United States Patent
Grunzweig et al.

(10) Patent No.: US 10,379,449 B2
(45) Date of Patent: Aug. 13, 2019

(54) IDENTIFYING PROCESS VARIATIONS DURING PRODUCT MANUFACTURE

(71) Applicant: KLA-TENCOR CORPORATION, Milpitas, CA (US)

(72) Inventors: Tzahi Grunzweig, Hillsboro, OR (US); Nadav Gutman, Zichron Ya'aqov (IL); Claire E. Staniunas, Forest Grove, OR (US); Tal Marciano, Zychron Yaacov (IL); Nimrod Shuall, Beaverton, OR (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/760,787

(22) PCT Filed: Feb. 7, 2018

(86) PCT No.: PCT/US2018/017273
§ 371 (c)(1),
(2) Date: Mar. 16, 2018

(87) PCT Pub. No.: WO2018/148318
PCT Pub. Date: Aug. 16, 2018

(65) Prior Publication Data
US 2019/0033730 A1  Jan. 31, 2019

Related U.S. Application Data

(60) Provisional application No. 62/457,781, filed on Feb. 10, 2017, provisional application No. 62/591,088, filed on Nov. 27, 2017.

(51) Int. Cl.
*G03F 7/20* (2006.01)
*H01L 21/66* (2006.01)
*G01N 21/01* (2006.01)

(52) U.S. Cl.
CPC ......... *G03F 7/70683* (2013.01); *G01N 21/01* (2013.01); *G03F 7/70641* (2013.01);
(Continued)

(58) Field of Classification Search
CPC ......... H01L 22/12; H01L 22/20; G01N 21/01; G01N 2021/0143; G01N 7/70641; G01N 7/70683
See application file for complete search history.

(56) References Cited

U.S. PATENT DOCUMENTS

2007/0222464 A1  9/2007  Honda et al.
2008/0062385 A1  3/2008  Klaassen
(Continued)

FOREIGN PATENT DOCUMENTS

WO        00022655 A1   4/2000

OTHER PUBLICATIONS

ISA/KR, International Search Report for PCT/US2018/017273 dated May 18, 2018.

*Primary Examiner* — Michelle M Iacoletti
(74) *Attorney, Agent, or Firm* — Hodgson Russ LLP

(57) ABSTRACT

Systems and method are presented for identifying process variations during manufacture of products such as semiconductor wafers. At a predetermined stage during manufacture of a first products, images of an area of the first product are obtained using different values of at least one imaging parameter. The images are then analyzed to generate a first contrast signature for said first product indicating variations of contrast with said at least one imaging parameter. At the same predetermined stage during manufacture of a second product, images of an area of said second product are obtained corresponding to said area of said first product using different values of said at least one imaging parameter. The images are analyzed to generate a second contrast
(Continued)

signature for said second product indicating variations of contrast with said at least one imaging parameter. The first and second contrast signatures are compared to identify whether a variation in process occurred between manufacture of said first and second products.

17 Claims, 8 Drawing Sheets

(52) U.S. Cl.
CPC .............. *H01L 22/12* (2013.01); *H01L 22/20* (2013.01); *G01N 2021/0143* (2013.01)

(56) References Cited

U.S. PATENT DOCUMENTS

| | | |
|---|---|---|
| 2009/0144691 A1 | 6/2009 | Rathsack et al. |
| 2016/0103946 A1 | 4/2016 | El Kodadi et al. |

IDENTIFYING PROCESS VARIATIONS DURING PRODUCT MANUFACTURE

CROSS REFERENCE TO RELATED APPLICATIONS

This application claims the benefit of U.S. Provisional Patent Application No. 62/457,781 filed Feb. 10, 2017 and U.S. Provisional Patent Application No. 62/591,088 filed Nov. 27, 2017, both of which are incorporated herein by reference in their entirety.

BACKGROUND OF THE INVENTION

1. Technical Field

The present invention relates to the field of quality control in manufacturing processes.

2. Discussion of Related Art

In manufacturing processes, quality control systems and procedures are used to identify variations in the process between the manufacture of one item and another in order to ensure consistency. Sometimes such variations are only apparent in the finished product or may not be apparent until after many sub-standard products have been produced. Semiconductor components, such as integrated circuits, may be manufactured in the form of a wafer containing many components. Semiconductor wafers, e.g. silicon wafers, may be manufactured in a series of layers each consisting of a pattern that must be accurately positioned with respect to patterns in the adjacent layers. The control of this positioning is called overlay control. In some semiconductor and lithography manufacturing processes, a metrology target is provided on the wafer for use in ensuring pattern alignment. The target may take the form of a set of cells, for example a 2×2 array of rectangular or square cells, two for measuring overlay in the X direction and two for measuring overlay in the Y direction. The target may include a diffraction grating. For example, each cell in a target may consist of a diffraction grating. A target may consist of a set of patterns, where each pattern may be printed on a different layer and may be oriented such as to provide measurement in different directions, typically X and Y.

In any manufacturing process, process variations may occur which may be undesirable. To take the example of lithographic processes, overlay measurement, e.g. measurement of pattern alignment, may not reveal a process variation that has occurred, such as a variation in thickness of an applied layer of material. In some instances a process variation may lead to incorrect overlay measurement. Therefore there is a need for better understanding of process variations and their effects.

SUMMARY OF THE INVENTION

The following is a simplified summary providing an initial understanding of the invention. The summary does not necessarily identify key elements nor limits the scope of the invention, but merely serves as an introduction to the following description.

Some embodiments of the present invention provide methods and systems for identifying process variations during manufacture of products such as semiconductor wafers. According to some embodiments of the invention, a "contrast signature" may be generated for a product, such as a wafer or part of a wafer, for example at a predetermined stage during manufacture. The contrast signature may be generated when a manufacturing process is believed to be operating as desired, for example to be used as a reference. A similar contrast signature may then be generated for another product, for example at the same stage of the manufacturing process, and the contrast signatures may be compared in order to identify whether a process variation has occurred.

A "contrast signature" is defined herein as a representation of variation of contrast in an image relative to at least one imaging parameter. Any known measure of image contrast may be used. The representation may be graphical, and e.g. displayed to a user, or it may be represented mathematically, for example as a vector, or in any other way in which it may be compared with another contrast signature, for example by a processor in a computing system. Thus according to some embodiments of the invention a process variation may be identified automatically and optionally an alert may be generated, or some remedial action may take place, in response to the identification of a variation.

Embodiments of the invention are not limited to semiconductor wafer production and may be used in the manufacture of many other products.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1A:
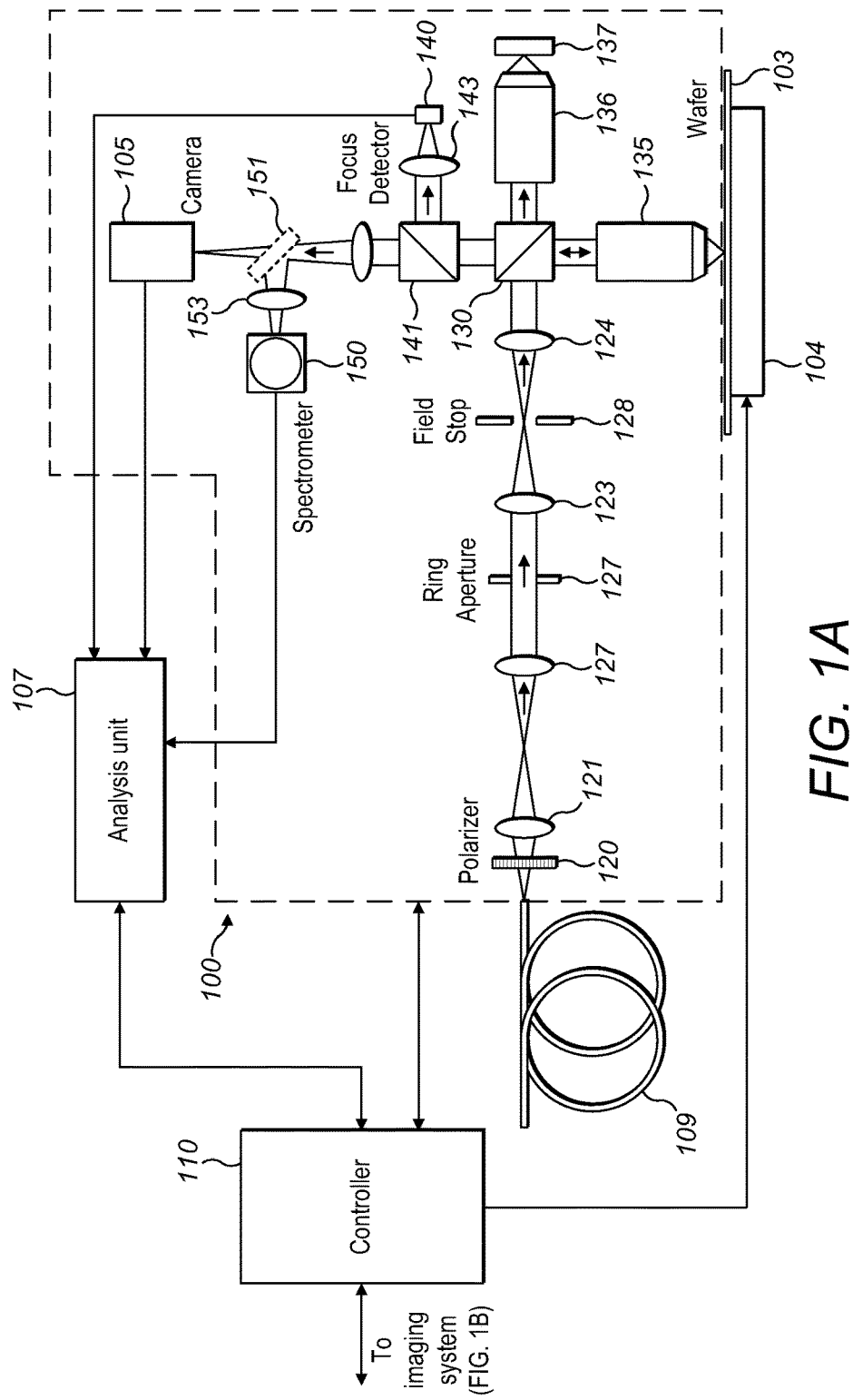
FIGS. 1A and 1B are schematic diagrams of a system according to some embodiments of the present invention.

Prior to the detailed description being set forth, it may be helpful to set forth definitions of certain terms that will be used hereinafter.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless otherwise stated, features described in relation to one or more embodiments of the invention may optionally be included in all other embodiments of the invention.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Figure 1B:
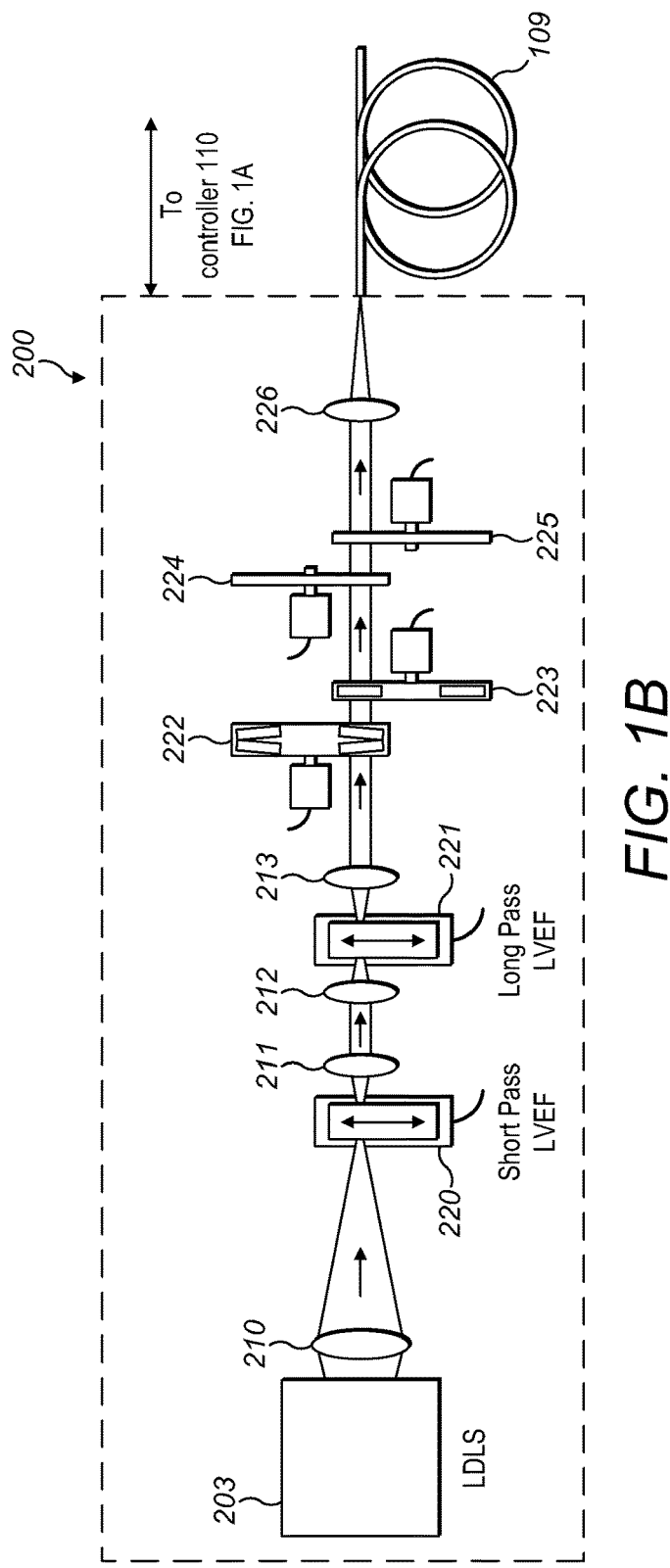

FIGS. 1A and 1B are schematic diagrams of a system according to some embodiments of the invention for use in manufacturing semiconductor wafers. Systems and methods as described herein may be used in the manufacture of other products, for example any products which may be imaged to generate a contrast signature as described further herein. The effectiveness of the contrast signature in identifying process variations may depend on the type of product. The system of FIGS. 1A and 1B may be used to obtain images of an area of a wafer surface using different values of one or more imaging parameters. Thus the system may be configured such that one or more imaging parameters is variable. The area may be a metrology target e.g. for overlay measurement, such as a diffraction pattern or grating.

FIG. 1A shows an imaging system 100 arranged to direct radiation towards the surface of a wafer and to receive radiation reflected from a wafer to produce images of the wafer, and FIG. 1B shows an illumination system 200 which may be used to supply radiation to the imaging unit of FIG. 1A.

In the imaging system 100 of FIG. 1A, radiation, such as visible light, is directed towards the surface of a product, in this illustration wafer 103, on a support 104. The radiation may be directed at a metrology target. Reflected radiation is received from the surface of the wafer 103 and used to produce images of the wafer, for example in a camera 105. The images may be analyzed in an analysis unit 107. The operation of the imaging system may be controlled by a controller 110.

The radiation may be supplied to the imaging system 100 by an optical fiber 109 and pass through polarizer 120 and lenses 121-124, to reach beam splitter 130. A ring aperture 127 may be positioned between lenses 122 and 123 and a field stop 128 may be positioned between lenses 123 and 124, whose functions will be understood by those skilled in the art. A beam splitter 130 may split the radiation such that one part of the radiation is directed via an objective lens system 135 to the wafer 103 and one different part of the radiation is directed via an objective lens system 136 to a mirror 137. The same pair of objective lens systems 135 and 136 may collect scattered radiation from the wafer 103 and reflected radiation from the mirror 137 and the same beam splitter 130 may combine the radiation from the wafer and the mirror to form a single radiation field whose details are sensitive to the distance between the objective 135 and the wafer 103 (the focus), in a way that allows the defocus to be deduced.

Some of the combined radiation may be directed to a focus detector 140, whose function is described further herein. For example some of the combined radiation may be directed to the focus detector 140 by a beam splitter 141 and lens 143. Some of the reflected radiation may be directed to a spectrometer 150. For example some of the reflected radiation may be directed to the spectrometer 150 by a beam splitter 151 and lens 153. The focus detector 140 may perform focus measurements and output signals indicative of those measurements to the analysis unit 107. Similarly the spectrometer 150 may perform spectral measurements and output signals indicative of those measurements to the analysis unit 107.

Camera 105 may be a charge coupled device or "CCD" array. Camera 105 may be arranged, or set, to form an image from the reflected radiation at the "image" plane, as is known in the art. For example the wafer 103 may include a diffraction pattern on its surface in which case the reflected radiation may be diffracted radiation from the surface of the wafer 103.

Various ones of the components forming part of the imaging system 100 of FIG. 1A, or the wafer support 104, may be moved with respect to each other, for example by one or more motors not shown and known to those skilled in the art. The operation of the imaging system 100, for example the operation of motors forming part of the imaging system 100, may be controlled by controller 110. The operation of controller 110 may be based in part on signals from analysis unit 107. Analysis unit 107 or controller 110 or both may comprise a computing system including on or more processors. For example a processor in analysis unit may generate and compare contrast signatures according to some embodiments of the invention.

According to some embodiments of the invention, images of a wafer may be obtained using different values of one or more imaging parameters. Thus, controller 110 may control imaging system 100 to vary one or more imaging parameters between successive image capturing operations, for example to form a series of images to be analyzed by analysis unit 107. Thus for example the controller 110 may control the polarizer 120 to change the polarization of the radiation between one image and another. The controller may control the position of any of the lenses, or the wafer support 104, for example lenses in objective lens system 135 with respect to each other or to wafer support 104, to vary the focus and thereby obtain a series of images each with a different degree of focus. The controller may control the the operation of the ring aperture 127 to vary the numerical aperture between one image and another. The ring aperture may be implemented as a double ring, described in more detail with reference to FIGS. 7A to 7C. Other imaging parameters which may be varied according to some embodiments of the invention include but are not limited to center wavelength of radiation used to illuminate the wafer and bandwidth of the radiation. It is also possible according to some embodiments of the invention to vary combinations of parameters in order to generate a contrast signature representing variation of contrast with a parameter combination.

Referring now to FIG. 1B, the illumination system 200 according to some embodiments of the invention comprises a source of radiation 203. This may be any suitable radiation source known to those skilled in the art. According to some embodiments of the invention, the source of radiation 203 may comprise multiple radiation sources of different wavelengths and/or bandwidths, from which one or more may be selected, for example in order to vary the wavelength and/or bandwidth used to illuminate a product, or target.

As shown in FIG. 1B, radiation from source 203 passes through a series of lenses 210-214 and filters 220-226 to optical fiber 109. The illumination system 200 may be operable to vary one or more imaging parameters, e.g. parameters which when varied cause a variation in an image captured by an image capturing device, e.g. using the radiation source 203 as a source of illumination. An example of an imaging parameter that may be varied by controlling the illumination system is the wavelength of the radiation. A wafer manufacturing control system may include a variable wavelength illumination system in which case some embodiments of the invention may be implemented by operating an existing system, e.g. existing hardware, in a novel way. According to some embodiments of the invention new hardware or software, including components operable to vary the wavelength of radiation used to illuminate a wafer to be imaged, may be provided.

In the system illustrated in FIG. 1B, filters 222-226 may comprise filters in an existing wafer manufacturing control system such as bandpass and gradient filters whose functions will be known to those skilled in the art. Filters 220 and 221 may be used to vary the wavelength of radiation delivered to imaging system 100 according to some embodiments of the invention, for example where this cannot be achieved by filters 222-226.

In practice an illumination system may use radiation polarized in different ways in which case differently polarized radiation may be conducted along different channels from the source 203 to the optical fiber 109. Only one channel is illustrated in FIG. 1B for simplicity but it will be appreciated that in a practical system a number of channels may be provided according to the number of polarizations.

According to some embodiments of the invention, the wavelength of radiation used to illuminate the product, e.g. wafer 103, may be varied in any known manner of wavelength variation. A system according to some embodiments of the invention may include mechanical apparatus to filter a narrow band of wavelengths of light from a wider band source. For example, a wide band radiation source may be mechanically distributed by means of a prism from which light in a particular wavelength band, or color, may be mechanically selected, for example using a shutter mechanism. In the example shown in FIG. 1B, filters 211 and 212 may be high pass and low pass filters respectively. Additionally or alternatively, filters 211 and 212 may be tunable as known in the art to vary the wavelength of radiation.

It will be appreciated to one skilled in optics that the order of some of the components shown in FIGS. 1A and 1B, such as lenses and beam splitters, may be varied whilst still enabling the system to operate as described herein. In particular, some of the components of the imaging system 100 as illustrated may form part of the illumination system 200 and some of the components of the illumination system 200 may form part of the imaging system 100.

According to some embodiments of the invention, for a particular wafer or wafer area at a particular point in a manufacturing process, variations of image contrast with an imaging parameter may be analyzed to generate a contrast signature. A contrast signature may be generated in the same way for a corresponding area of another wafer at the same point in the manufacturing process. The contrast signatures may be compared to identify a variation in the manufacturing process.

Figure 2A:
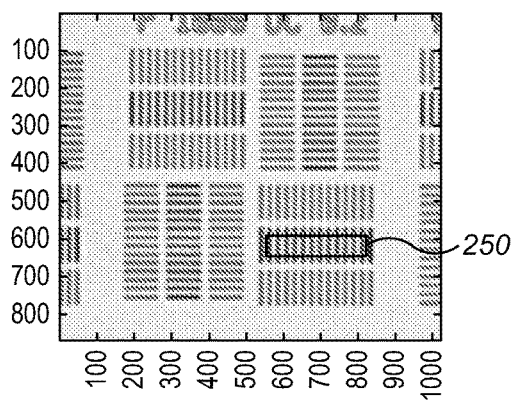
FIG. 2A is an image of a metrology target.
Figure 2B:
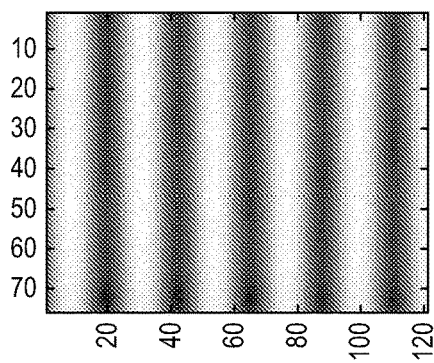
FIG. 2B is an enlarged image of part of the target and FIG. 2C is a graph of variation of intensity along a line crossing the image of FIG. 2B, according to some embodiments of the invention.
Figure 2C:
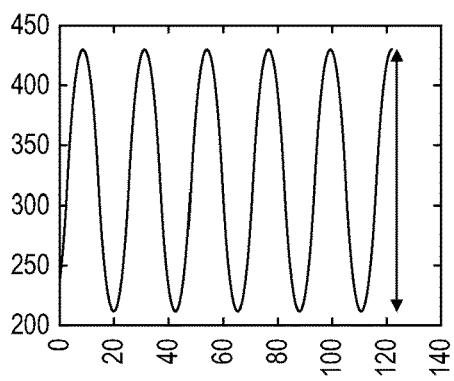

FIGS. 2A-2C are illustrations for the purpose of explaining the use of contrast according to some embodiments of the invention.

FIG. 2A is an image of a metrology target of a kind known in the art, which may be provided on a wafer for the purpose of overlay measurement. FIG. 2B is an enlarged view of a component 250 in FIG. 2A, which may for example be associated with a particular layer. It can be seen in FIG. 2B that the component that has a visual oscillation between roughly two values ("black" and "white"). FIG. 2C is a one-dimensional representation of target component 250, termed a "kernel", formed by adding the rows of the image of FIG. 2B (or columns depending on the orientation of the component, or more generally region of interest). A kernel such as that shown in FIG. 2C has a structure of peaks and valleys corresponding to maximum intensity I_max, and minium intensity I_min.

Contrast of a repeating pattern is a measure of the visibility of the pattern. A standard way of quantifying or measuring the contrast is by the "Michelson contrast" definition:

$$\text{Contrast} = (I\_\text{max} - I\_\text{min})/(I\_\text{max} + I\_\text{min}) \tag{1}$$

where I_max and I_min represent the highest and lowest luminance. Quantifying contrast according to this equation provides an absolute measure of contrast.

For the purpose of some embodiments of this invention, it is useful to assign a sign or direction, positive or negative, to the contrast. This is referred to herein as "signed contrast" and is useful in identifying "contrast reversal" as described further herein. For example, if the arrangement of the peaks and valleys is such that the first is the I_max, then the sign + may be assigned to the Michelson contrast. If the first peak or valley is the I min then the sign − may be assigned to the Michelson contrast. Thus in any of the embodiments of the invention described herein, the contrast signature may optionally indicate the sign or direction of the contrast. In other words the contrast signature may indicate variations in the signed contrast rather than the absolute value or modulus of the contrast.

The allocation of a + or − to the contrast measurement as described above is one of several possibilities for differentiating contrast measurements. Any other scheme for differentiation may be used. The signed contrast indicates whether the contrast is positive or negative and can therefore be used to identify contrast reversal, where contrast changes from positive to negative or vice versa, discussed further herein.

Embodiments of the invention are not limited to quantifying contrast using the above equations. There are several ways of quantifying contrast and any of them may be used.

In FIG. 2B a region of interest is seen with a positive contrast according to the foregoing definition of positive or negative contrast. If the black and white bars were reversed this would be determined to be negative contrast. The positive and negative values may be assigned the opposite way provided that the inverse is oppositely signed to the original of any kernel.

The contrast of an image is dependent on imaging parameters discussed with reference to FIGS. 1A and 1B including but not limited to illumination details such as numerical aperture, polarization, spatial content (e.g. arrangement of bars), color (which may be loosely defined as the spectral distribution—which can be characterized by wavelength and bandwidth). It has been discovered that some variations in a semiconductor manufacturing process result in a difference in relationship between contrast and an imaging parameter. Therefore according to some embodiments of the invention, this relationship may be determined for one wafer and the determination may be repeated for another wafer to identify whether a variation in process has occurred. This relationship may be determined through the generation of a contrast signature for a wafer or wafer area representing variation of contrast in an image relative to at least one imaging parameter.

The contrast signature may represent variation of contrast in an image relative to at least one imaging parameter. The representation may be graphical, for example a map or graph, and may according to some embodiments of the invention be displayed to a user. Additionally or alternatively, the signature may be a mathematical representation, such as a vector or equation or other mathematical expression. A contrast signature may be in any form in which it may be compared with another contrast signature, for example but not limited to visually by a user or by a processor in a computing system.

A contrast signature may be a characteristic of a wafer at the point in time or period of time of capture of the images from which it is generated.

The contrast signature may comprise one or more features, and according to some embodiments of the invention the identification of a process variation may comprise detecting a difference in one or more features in the contrast signature, such as a shift detectable when comparing one signature to another. For example, if the contrast signature comprises a graph, the feature may comprise a peak or trough or zero crossing point. In the particular case where the imaging parameter is focus, a feature in the signature may result from contrast reversal. Other features in a contrast signature that may be used to compare one with another may include but are not limited to the position of the maximum of a gradient of the contrast/signed contrast, maximum contrast position, or some specific value of contrast (i.e. contours of the contrast) and any other characterization of a contrast map by "template" features.

Contrast reversal is a known effect, in which as a result of de-focusing the image, a periodic feature undergoes inversion: e.g. in the example of FIG. 2B the black stripes turn to white and simultaneously the white stripes turn to black. The change of contrast as defocusing progresses is continuous, and therefore there is a point in which both black and white turn to grey—and the contrast becomes zero. This is the contrast-reversal point. Referring to FIG. 1A, defocusing may be achieved for example by varying the distance between objective lens system 135 and wafer 103. Starting from a distance suitable to produce an image as shown in FIG. 2B, the distance may be increased or decreased continually and either way a contrast reversal may occur in the image at a particular distance.

Figure 3C:
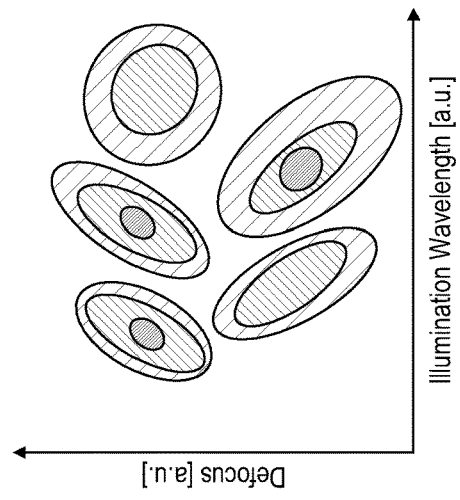
FIG. 3C shows only the contrast reversal curves according to some embodiments of the invention.
Figure 3B:
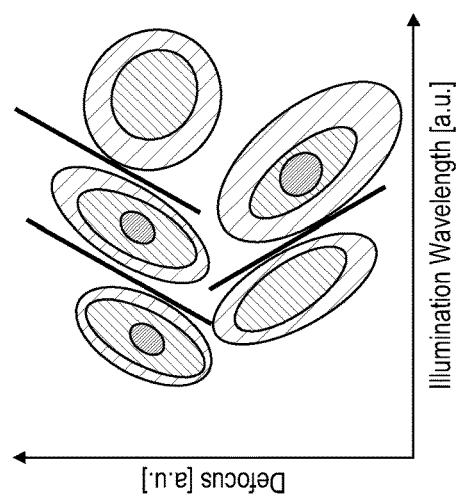
FIG. 3B is shows the map of FIG. 3A with contrast reversal lines added.
Figure 3A:
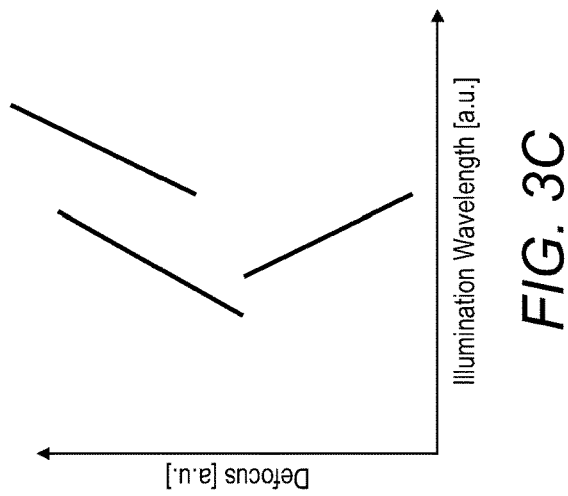
FIG. 3A is schematic example of a contrast map.

FIGS. 3A-3C illustrate embodiments of the invention in which a contrast signature may be generated from images in which two imaging parameters are varied. In the particular embodiment shown in the figures the two imaging parameters are focus, measured for example in terms of a distance between optical components which is varied, and wavelength. The obtaining, e.g. capturing, of images using different values of more than one imaging parameter may be achieved in various ways. For example, a component distance may be set, images at various wavelengths may be obtained, the component distance may be incremented and the obtaining images at various wavelengths may be repeated. Referring to FIG. 1, this variation of imaging parameter may be controlled by controller 110 controlling the operation of the illumination system 200 and the imaging system 100. Throughout the process the wafer may be stationary in lateral directions, e.g. not moved laterally, to ensure that each image is an image of the same portion of the wafer. This process may be repeated on a similar wafer undergoing the same process at the same stage in the process, at a later time, for example after several wafers have been manufactured to the same process, to determine whether a process variation occurred.

After obtaining images at various values of two imaging parameters, a contrast signature may be generated in the form of a three dimensional map, where imaging parameters and the contrast are the three dimensions, for example the map x and y axes may the imaging parameters and the contrast may be represented in another dimension, for example the z axis or by color representation or in any other way. FIG. 3A shows a schematic example of such a map where the imaging parameters are illumination wavelength and focus, determined for example by a distance, and contrast is represented in a third axis, in the illustrated example grayscale. The result is a contour map. In other embodiments of the invention, different imaging parameters may be varied and therefore these different imaging parameters may be indicated on the axes.

It will be appreciated that it is possible according to some embodiments of the invention to compare a contour map of the kind shown in FIG. 3A, or any other three dimensional representation, with another generated from images of the corresponding area of another wafer at the same stage of manufacturing, in order to identify a process variation between the manufacture of the two wafers. In other words a map or three dimensional representation of the kind shown in FIG. 3A may serve as a contrast signature. Any known techniques for the comparison of images may be used in order to identify a process variation, including correlation techniques.

According to some embodiments of the invention the contrast signature may be simplified for the purpose of comparison. In the map of FIG. 3B contrast reversal curves have been added. These correspond to points where the contrast has reversed as described elsewhere herein. In the schematic example of FIG. 3B the contrast reversal curves are straight lines. FIG. 3C is a graph showing only the contrast reversal lines, other contrast data has been removed.

Figure 4C:
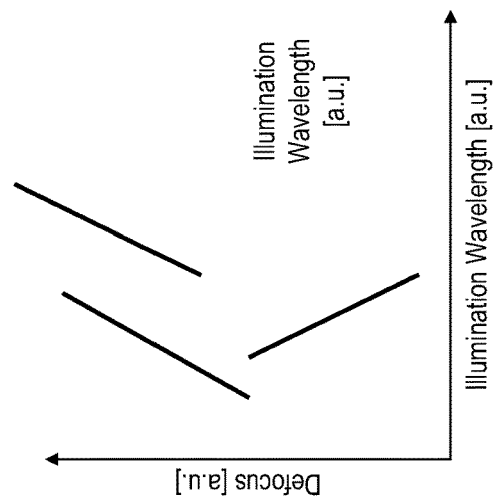
FIGS. 4A, 4B and 4C schematically illustrate a shift in contrast reversal lines according to some embodiments of the invention.
Figure 4B:
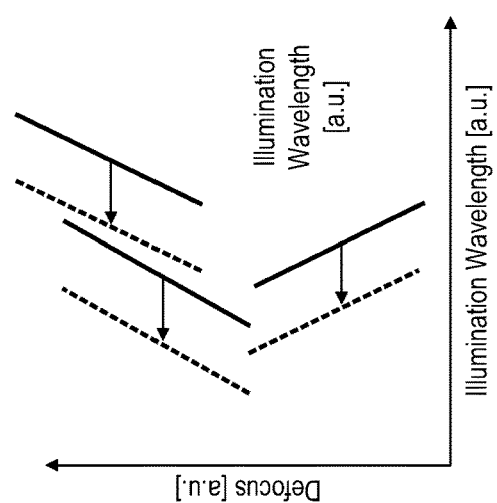
Figure 4A:
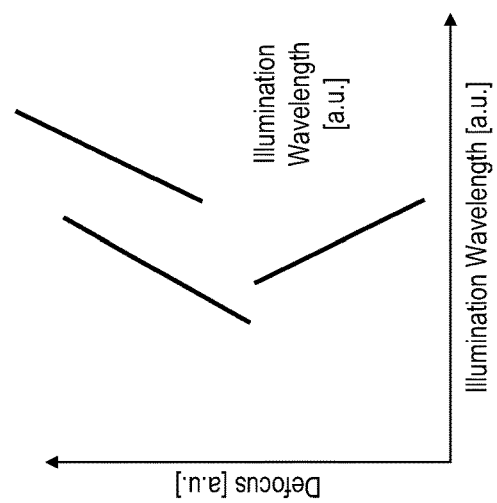

FIGS. 4A to 4C illustrate schematically how a process variation may be identifiable from a contrast signature.

Minute process variations such as might occur in a semiconductor wafer manufacturing process may result in an alteration of a contrast signature for the wafer surface, or part of the wafer surface. The same may occur in other manufacturing processes. The nature of the signature change may be related to the type of variation. For example, if the contrast signature is a graph of the kind shown in FIG. 3C, some process variations may result in a shift of a feature of the contrast signature with respect to one or more imaging parameters.

FIG. 4A is a graph corresponding to the graph of FIG. 3C. A process variation of a particular type may cause a shift in contrast reversal curves with respect to an imaging parameter, e.g. wavelength, to a new position shown in FIG. 4B. A signed contrast signature generated for a wafer produced by a process that is subject to the variation may appear as shown in FIG. 4C. The contrast signatures of FIGS. 4A and 4C may be readily compared, for example automatically in a computing system, to identify the process variation, following which remedial action may be required.

It should be noted that embodiments of the invention are not limited to identifying process variations that may occur over time, for example due to wearing of parts of machinery. Embodiments of the invention may be used to identify variations in, or differences between, processes that are taking place at the same time, for example processes operating in parallel.

Figure 5C:
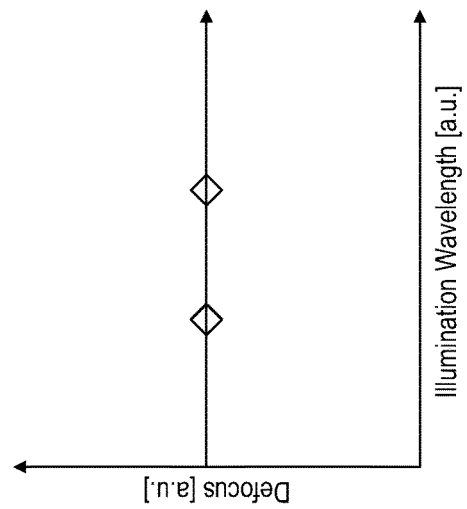
FIG. 5C shows only the selected points according to some embodiments of the invention.
Figure 5B:
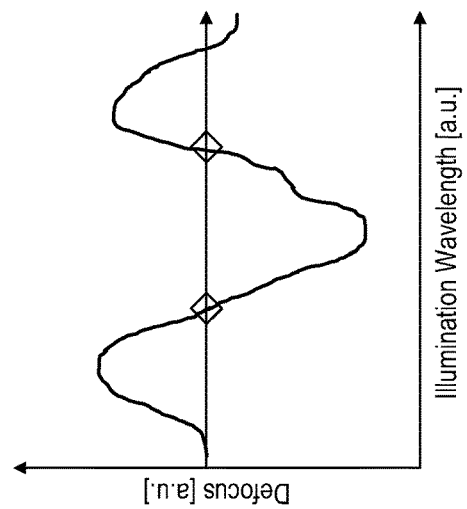
FIG. 5B is a graph similar to FIG. 5A with particular points indicated.
Figure 5A:
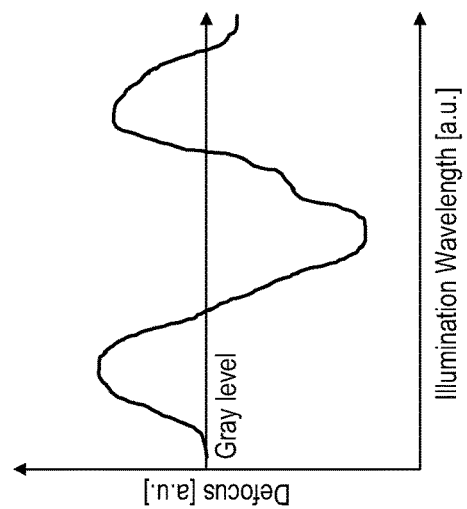
FIG. 5A is a schematic graph showing variation of contrast with wavelength.

A contrast signature may be generated based on the variation of contrast with only one imaging parameter. An example is shown in FIGS. 5A-5C. FIG. 5A is a graph showing variation of contrast with illumination wavelength which may form a contrast signature. In this example the signed contrast is determined in a manner which indicates whether the contrast is positive or negative with respect to a predetermined gray level. FIG. 5A approximates a graph that might be derived from the map of FIG. 4A. It will be apparent from a comparison of FIGS. 4A and 5A that the zero crossing points of FIG. 5A correspond to the contrast reversal lines of FIG. 4A.

As with the maps of FIGS. 4A-4C, a contrast signature as shown in FIG. 5A may be reduced to one or more features. FIG. 5B shows the zero crossing points on the graph of FIG. 5A and FIG. 5C shows only the zero crossing points which may be sufficient to form a contrast signature. The zero crossing points may be shifted between one wafer and another in the same way as the contrast reversal curves and therefore used to identify a process variation.

It can be seen from FIG. 5B that the exact position where contrast reversal occurs is particularly sensitive to a change in the imaging parameter. A small change in wavelength will lead to a large change in contrast. The same applies to any area on a graph or map in which the rate of change of contrast is relatively large. Therefore the choice of points or areas with a high rate of change such as contrast reversal points for comparing one signature with another provides a highly sensitive measurement of difference in contrast signature, which can be used to identify minute variations in process.

The interest in illumination parameters that are most sensitive to change is in contrast to overlay measurement techniques, where high contrast images are desired and imaging parameters may be chosen to have the least effect on contrast. For example, referring again to FIG. 5B, the choice of wavelength for capturing images for overlay measurement is likely to be at any of the peaks in the graph where the rate of change of contrast with wavelength is lowest.

Identification of process variations through the use of contrast signatures, according to some embodiments of the invention, may be used to identify process variations that are not detectable from overlay measurement, such as but not limited to variations in layer thickness and variations in optical properties of materials such as index of refraction.

Figure 6:
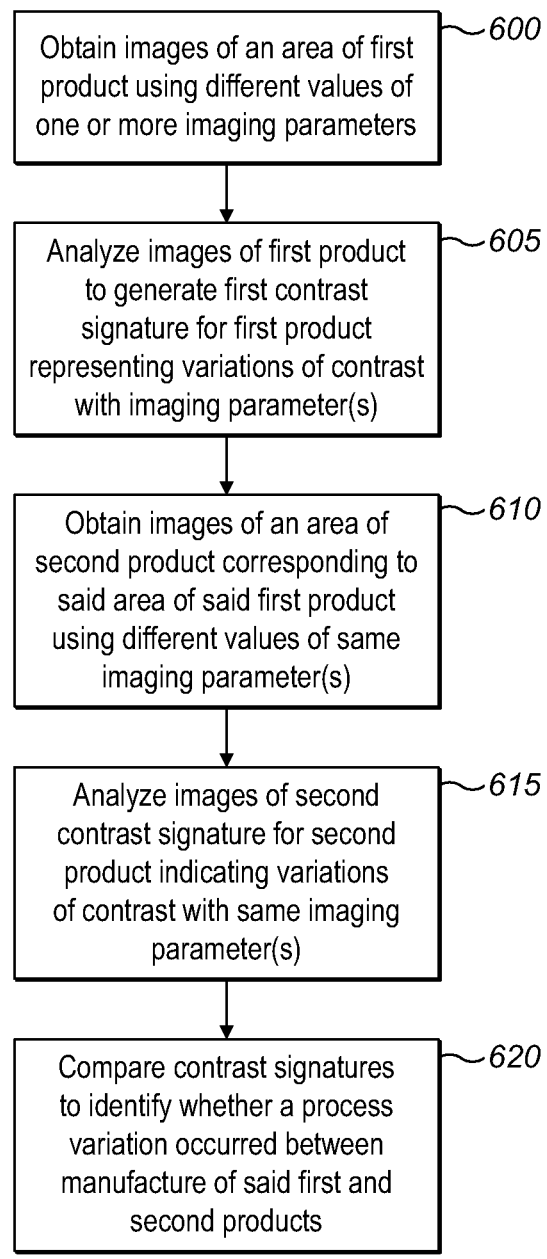
FIG. 6 is a flowchart of a method according to some embodiments of the invention.

FIG. 6 is a flowchart of a method according to some embodiments of the invention. The method of FIG. 6 begins at operation 600, at a predetermined stage in the manufacture of a first product, with obtaining images of an area of the product using different values of one or more imaging parameters, such as focus or wavelength or both. The terms "first", "second" etc. are used here simply to differentiate one product from another and do not necessarily imply any temporal or other order. The images may be analyzed at operation 605 to generate a first contrast signature for the first product, representing variation of contrast with the one or more imaging parameters.

At the same predetermined stage in the manufacture of a second product, which may be later or earlier or running in parallel with the manufacture of the first product, another operation of obtaining images is performed at operation 610 using different values of the same one or more imaging parameters. The images obtained at operation 610 are analyzed at operation 615 to generate a second contrast signature for the second product indicating variations of contrast with the one or more imaging parameters.

According to some embodiments of the invention, the products are manufactured in lots and the first and second products are from different lots.

The contrast signatures are compared at operation 620 to identify whether a variation in process occurred between manufacture of the first and second products. According to some embodiments of the invention, an alert may be generated if a process variation of more than a predetermined magnitude is identified. For example, a difference in contrast signature, such as a difference in position of one or more features in the contrast signatures, may be compared to a predetermined threshold, and an alert may be generated if the difference exceeds the threshold.

Embodiments of the invention may also be used to monitor the progress of a process variation and for example plot its progress over time. This can then be correlated to process control parameters, such as but not limited to temperature of the wafer during etch, for example by means of graphs. This may be used to analyze the root cause of a variation.

The obtaining of images by camera 105 may be performed under the operation of controller 110 and the analysis may be performed in analysis unit 107, possibly controlled by controller 107. It may be possible to modify existing systems to implement methods according to some embodiments of the invention. Therefore some embodiments of the invention may comprise a computer readable medium, either transitory or non transitory, comprising instructions which when implemented in a controller in a product manufacturing system, cause the system to operate according to the methods described herein.

Operations 600-620 may be performed during manufacture of different pairs of first and second wafers to regularly monitor possible manufacturing process variations.

Figure 7A:
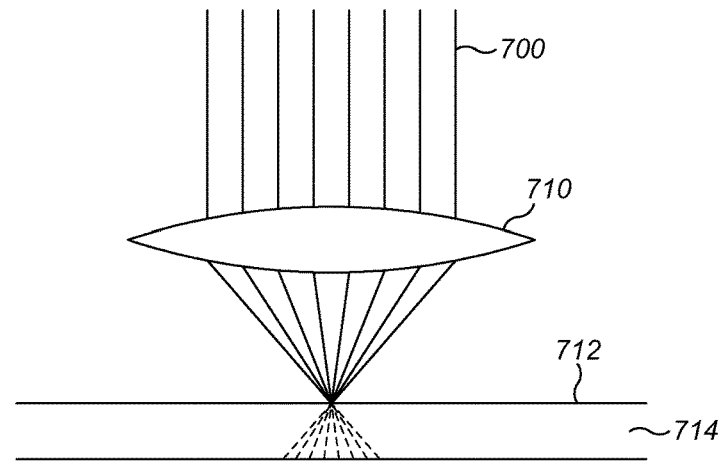
FIGS. 7A-7C are schematic diagrams illustrating the possibility of using numerical aperture as a variable imaging parameter according to some embodiments of the invention.
Figure 7B:
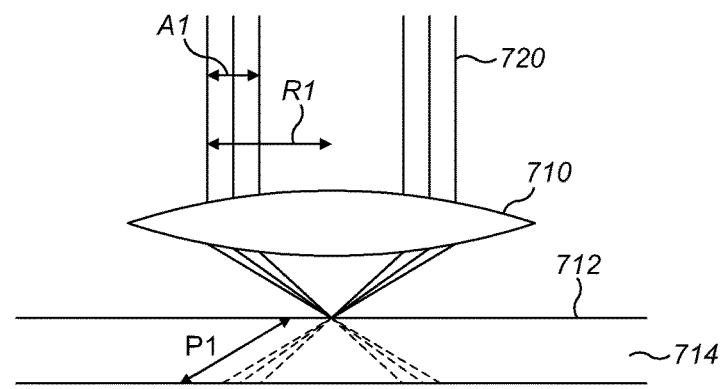
Figure 7C:
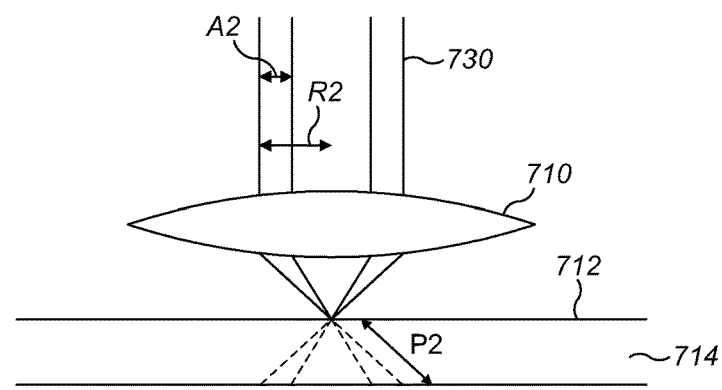

FIG. 7A-7C are schematic diagrams illustrating the use of numerical aperture as a variable imaging parameter according to some embodiments of the invention. For example, the imaging parameter mentioned in connection with FIG. 6 may be the numerical aperture. FIG. 7A shows a collimated beam of radiation 700 focused by a lens 710 onto the surface 712 of a layer 714 of a wafer such as wafer 103. It is clear from this figure that the length of the path of the radiation through the layer 714 depends on the angle of incidence. Radiation entering the layer normal to the surface has the shortest path through the layer, and the path length increases from the center of the beam 700 outwardly.

The numerical aperture in an optical system may define the proportion of a radiation beam that passes through any part of the system. Thus, the numerical aperture may be varied to exclude part of the radiation beam. Varying the numerical aperture may have the effect of varying the range of angles of incidence of the radiation on the surface of the product. According to some embodiments of this invention, the imaging parameter that is varied in operation 605 may comprise incident angle or range of incident angles of radiation on the surface of the product, varied for example by varying the numerical aperture to limit the range of incident angles. This variation may be used to generate different contrast signatures in a similar manner to variation of wavelength described herein.

The limitation of the range of incident angles may, for angular ranges excluding normal, result in the incident radiation forming an annular beam. FIGS. 7B and 7C illustrate the same arrangement as FIG. 7A except that the beam 700 is reduced to annular beams 720 and 730 of different radius R1 and R2 respectively and width A1 and A2 respectively which may be equal. The maximum path length P1 of beam 720 through the layer 714 is longer than the maximum path length P2 of beam 730 through the layer 714. It will be appreciated by one skilled in the art that varying the path length through a very thin target such as in semiconductor manufacturing may have a similar effect to varying the wavelength of the incident radiation. Therefore varying the angle of incidence may be used to generate a similar contrast signature to that shown in FIGS. 3A-3C.

As noted elsewhere herein, other imaging parameters than wavelength and aperture or incident angle may be varied according to embodiments of the invention in order to generate contrast signatures.

Systems and methods according to some embodiments of the invention may be used to identify process variations that may then be investigated and if necessary rectified. For example, a variation may be quantified, such as amount of shift in contrast reversal with respect to an imaging parameter, and it may be determined that a variation with a quantity more than a threshold requires investigation. The nature of a variation may not be immediately apparent from a difference in contrast signature, and it may be necessary to perform additional measurements on one or both of the products from which the contrast signature was obtained in order to determine what the variation was.

However once the nature of the variation, e.g. increase or decrease in layer thickness, has been determined, this may be used to build up a bank of knowledge correlating types of difference in contrast signature with types of process variation, and possibly also to relate amount of difference in contrast signature to some quantity variation in the process such as layer thickness. Other process variations that may be identified include but are not limited to composition of a layer and optical parameters of a layer. According to some embodiments of the invention, a process variation may be identified, for example from a change in contrast signature of an amount greater than a predetermined threshold. Optionally an alert may be generated in response to identification of a process variation, for example to prompt an operator, e.g. human, to initiate remedial action.

The identification of a process variation may be followed by performing one or more measurements on a product to determine the nature of the variation. This determination may be used to automatically identify the nature of a variation identified in a future process. Thus according to some embodiments of the invention, the nature of a process variation may be automatically determined from a difference in contrast signature. Additionally or alternatively, the quantity of a variation may be determined from the amount of a difference in contrast signature. One difference discussed herein is a shift in contrast reversal. Embodiments of the invention are not limited to this difference and other differences in contrast signature may be identified and attributed to other variations in a manufacturing process. Historical data from previous methods may be used to attribute differences in contrast signatures of various kinds and optionally amounts to process variations of different kinds and optionally amounts. According to some embodiments of the invention, machine learning may be used to improve the reliability of attributions of differences to variations.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of identifying process variations during a product manufacturing process comprising:
   at a predetermined stage during manufacture of a first product:
   obtaining, using an imaging system, images of an area of said first product using different values of at least one imaging parameter;
   analyzing said images of said area of said first product to generate a first contrast signature for said first product representing variations of contrast of said images of said area of said first product with said at least one imaging parameter;
   at the predetermined stage during manufacture of a second product:
   obtaining images of an area of said second product corresponding to said area of said first product using different values of said at least one imaging parameter;
   analyzing said images of said area of said second product to generate a second contrast signature for said second product representing variations of contrast of said images of said area of said first product with said at least one imaging parameter; and
   comparing said first and second contrast signatures to identify whether a variation in process occurred between manufacture of said first and second products.

2. The method of claim 1 wherein said at least one imaging parameter comprises any one or more of:
   numerical aperture of the imaging system;
   wavelength of the imaging radiation;
   focus of the imaging system; or
   polarization of the imaging raditation.

3. The method of claim 2 wherein said identifying further comprises detecting a shift in one or more features in said first and second contrast signatures with respect to said at least one imaging parameter.

4. The method of claim 1 wherein said at least one imaging parameter comprises two imaging parameters.

5. The method of claim 4 wherein said two imaging parameters comprise focus of the imaging system and wavelength of the imaging radiation.

6. The method of claim 4 wherein said identifying further comprises detecting a shift in one or more features in said first and second contrast signatures with respect to said at least one imaging parameter.

7. The method of claim 1 wherein said identifying further comprises detecting a shift in one or more features in said first and second contrast signatures with respect to said at least one imaging parameter.

8. The method of claim 1 wherein said first and second signatures each comprise a contrast map.

9. The method of claim 1 wherein the first and second contrast signatures comprise one or more features including the values of the at least one imaging parameter at which the rate of change of contrast is highest.

10. The method of claim 1 wherein said analyzing comprises assigning a sign to measurements of contrast whereby said first and second contrast signatures identify contrast reversal.

11. The method of claim 1 wherein first and second contrast signatures comprise one or more features including the values of the at least one imaging parameter at which the contrast changes from positive to negative or vice versa.

12. The method of claim 1 wherein said area comprises a target for overlay measurement.

13. The method of claim 12 wherein said target comprises a diffraction grating.

14. The method of claim 1 wherein the first and second products are manufactured in lots and said first and second products are from different lots.

15. The method of claim 1 comprising repeating said obtaining, analyzing and comparing during manufacture of additional first and second products to regularly monitor possible manufacturing process variations.

16. The method of claim 1 wherein the first and second products are semiconductor wafers.

17. A system for identifying process variations during a product manufacturing process, the system comprising:
   an illumination system and an imaging system, the illumination system including a
   radiation source and the imaging system being arranged to direct radiation from the
   illumination system towards a surface of a product and to receive radiation from the
   illumination source reflected from the product to produce images of the product;
   a control unit arranged to control the imaging system or the illumination system or both to obtain images of first and second products at a predetermined stage of manufacture using different values of at least one imaging parameter;

an image analysis unit configured to analyze said images to generate respective contrast signatures for said first and second products representing variations of contrast with said at least one imaging parameter, and to compare said first and second contrast signatures to identify whether a variation in process occurred between manufacture of said first and second products.

* * * * *